United States Patent
Miike et al.

(10) Patent No.: US 9,950,313 B2
(45) Date of Patent: Apr. 24, 2018

(54) METHOD FOR PRODUCING OXIDE CATALYST, AND METHOD FOR PRODUCING UNSATURATED NITRILE

(71) Applicant: ASAHI KASEI KABUSHIKI KAISHA, Tokyo (JP)

(72) Inventors: Satoshi Miike, Tokyo (JP); Eri Tateno, Tokyo (JP); Yusuke Ishii, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/563,381

(22) PCT Filed: Mar. 30, 2016

(86) PCT No.: PCT/JP2016/060398
§ 371 (c)(1),
(2) Date: Sep. 29, 2017

(87) PCT Pub. No.: WO2016/159085
PCT Pub. Date: Oct. 6, 2016

(65) Prior Publication Data
US 2018/0085737 A1    Mar. 29, 2018

(30) Foreign Application Priority Data

Mar. 31, 2015  (JP) ................. 2015-073794

(51) Int. Cl.
| C07C 253/24 | (2006.01) |
| C07C 253/26 | (2006.01) |
| B01J 23/30  | (2006.01) |
| B01J 23/00  | (2006.01) |
| B01J 37/08  | (2006.01) |
| B01J 35/02  | (2006.01) |
| B01J 37/04  | (2006.01) |

(52) U.S. Cl.
CPC ............ *B01J 23/30* (2013.01); *B01J 23/002* (2013.01); *B01J 35/023* (2013.01); *B01J 37/04* (2013.01); *B01J 37/08* (2013.01); *C07C 253/24* (2013.01); *B01J 2523/00* (2013.01)

(58) Field of Classification Search
CPC ........................... C07C 253/24; C07C 253/26
USPC ........................................................ 558/319
See application file for complete search history.

(56) References Cited

U.S. PATENT DOCUMENTS

| 2006/0235238 A1 | 10/2006 | Komada et al. |
| 2014/0194642 A1 | 7/2014  | Endo et al.   |
| 2015/0231604 A1 | 8/2015  | Ishii et al.  |

FOREIGN PATENT DOCUMENTS

| CN | 101279252       | * 10/2008 |
| JP | 2000-070714 A   | 3/2000    |
| JP | 2002-219362 A   | 8/2002    |
| JP | 2002-292284 A   | 10/2002   |
| JP | 2003-3202488 A  | 11/2003   |
| WO | WO 2004-108278 A1 | 12/2004 |
| WO | WO 2012/144369 A1 | 10/2012 |
| WO | WO 2014/050615 A1 | 4/2014  |

OTHER PUBLICATIONS

CN 101279252 translation, 2008.*
International Preliminary Report on Patentability and English translation of the Written Opinion of the International Searching Authority (Forms PCT/IB/326, PCT/IB/373 and PCT/ISA/237) issued in International Application No. PCT/JP2016/060398 dated Oct. 12, 2017.
International Search Report for PCT/JP2016/060398 (PCT/ISA/210) dated May 31, 2016.

* cited by examiner

*Primary Examiner* — Sun Jae Yoo
(74) *Attorney, Agent, or Firm* — Birch, Stewart, Kolasch & Birch, LLP

(57) ABSTRACT

The present invention provides a method for producing an oxide catalyst comprising Mo, V, Sb, and Nb for use in a gas-phase catalytic oxidation reaction or a gas-phase catalytic ammoxidation reaction of propane or isobutane, the method comprising: a preparation step of preparing a first aqueous mixed solution containing Mo, V, and Sb; a mixing step of mixing the first aqueous mixed solution with a support raw material comprising silica sol, and a Nb raw material to obtain a second aqueous mixed solution; a drying step of drying the second aqueous mixed solution to obtain a dry powder; and a calcination step of calcining the dry powder to obtain the oxide catalyst, wherein the support raw material comprises 25% by mass or more, based on $SiO_2$, of the silica sol having an average primary particle size of 3.0 nm or larger and smaller than 11 nm based on a total amount of the support raw material, and the silica sol comprises 55% or more of silica sol particles having a primary particle size of smaller than 11 nm.

7 Claims, No Drawings

METHOD FOR PRODUCING OXIDE CATALYST, AND METHOD FOR PRODUCING UNSATURATED NITRILE

TECHNICAL FIELD

The present invention relates to a method for producing an oxide catalyst, and a method for producing unsaturated nitrile.

BACKGROUND ART

General commercially available unsaturated nitrile is currently industrially produced, mainly, by the catalytic ammoxidation reaction of olefin, ammonia, and oxygen. On the other hand, methods which involve using an alkane such as propane or isobutane as a raw material instead of the olefin and performing gas-phase catalytic ammoxidation reaction to produce unsaturated nitrile corresponding to the raw material have received attention in recent years, and many catalysts for use in such methods have also been proposed.

For example, Patent Literature 1 describes a method for producing a catalyst for the gas-phase catalytic oxidation or gas-phase catalytic ammoxidation of propane or isobutane, wherein the catalyst contains less scattering antimony, offers a high yield of unsaturated nitrile, and exhibits a high space time yield.

Patent Literature 2 describes a production method using a silica-supported catalyst in the production of unsaturated nitrile by the gas-phase catalytic ammoxidation reaction of propane or isobutane, or unsaturated carboxylic acid by the gas-phase catalytic oxidation reaction thereof, wherein the catalyst is supported by 20 to 60% by mass of silica and satisfies a pore volume of 0.15 cm³/g or larger, and powder silica having an average primary particle size of 50 nm or smaller is used as at least a portion of a silica raw material.

Patent Literature 3 states that pores formed by silica are optimized by calcination using in combination sol and powder silica which differ in primary particle size, to thereby improve the performance of an ammoxidation catalyst and efficiently obtain a product of interest.

CITATION LIST

Patent Literature

Patent Literature 1: Japanese Patent Laid-Open No. 2000-70714
Patent Literature 2: Japanese Patent Laid-Open No. 2002-219362
Patent Literature 3: International Publication No. WO 2012/144369

SUMMARY OF INVENTION

Technical Problem

Although the catalyst production methods described in Patent Literatures 1 to 3 produce a catalyst for ammoxidation reaction that can withstand specific conditions, the obtained catalyst offers an industrially insufficient yield of unsaturated nitrile when used, and does not have sufficiently high activity.

Thus, an object of the present invention is to provide a method for producing an oxide catalyst that eliminates the need of introducing complicated steps and changing facilities and can offer a high yield of unsaturated nitrile.

Solution to Problem

The present inventors have conducted diligent studies to solve the problems of the conventional techniques described above, and consequently completed the present invention by finding that use of a method for producing an oxide catalyst for use in specific reaction eliminates the need of introducing complicated steps and changing facilities and can produce a high yield of unsaturated nitrile, the method comprising a specific preparation step, mixing step, drying step, and calcination step, wherein a support raw material used in the mixing step comprises specific silica sol in a predetermined range of an amount.

Specifically, the present invention is as follows:

[1]
A method for producing an oxide catalyst comprising Mo, V, Sb, and Nb for use in a gas-phase catalytic oxidation reaction or a gas-phase catalytic ammoxidation reaction of propane or isobutane, the method comprising:

a preparation step of preparing a first aqueous mixed solution containing Mo, V, and Sb;

a mixing step of mixing the first aqueous mixed solution with a support raw material comprising silica sol, and a Nb raw material to obtain a second aqueous mixed solution;

a drying step of drying the second aqueous mixed solution to obtain a dry powder; and a calcination step of calcining the dry powder to obtain the oxide catalyst, wherein the support raw material comprises 25% by mass or more, based on SiO$_2$, of the silica sol having an average primary particle size of 3.0 nm or larger and smaller than 11 nm based on a total amount of the support raw material, and the silica sol comprises 55% or more of silica sol particles having a primary particle size of smaller than 11 nm.

[2]
The method for producing the oxide catalyst according to [1], wherein the oxide catalyst has a composition represented by following formula (1):

$$MoV_aSb_bNb_cZ_dO_n \qquad (1)$$

wherein Z represents at least one element selected from the group consisting of W, La, Ce, Yb, and Y; a, b, c, and d represent values in ranges of 0.01≤a≤0.35, 0.01≤b≤S 0.35, 0.01≤c≤0.20, and 0.00≤d≤0.10, respectively; and n represents a value that satisfies balance among valences.

[3]
The method for producing the oxide catalyst according to [2], wherein in the formula (1), (a/b) is 0.50 or more and 0.98 or less.

[4]
The method for producing the oxide catalyst according to any of [1] to [3], wherein the oxide catalyst comprises 30% by mass or more and 70% by mass or less of the support based on the total amount of the oxide catalyst.

[5]
The method for producing the oxide catalyst according to any of [1] to [4], wherein the support raw material further comprises powder silica.

[6]
The method for producing the oxide catalyst according to any of [1] to [5], wherein the support raw material comprises 30% by mass or more and 70% by mass or less, based on SiO$_2$, of the silica sol based on the total amount of the support raw material.

[7]

A method for producing unsaturated nitrile, comprising a production step of producing unsaturated nitrile by a gas-phase catalytic ammoxidation reaction of propane or isobutane in presence of an oxide catalyst produced by the method for producing the oxide catalyst according to any of [1] to [6].

Advantageous Effects of Invention

The method for producing an oxide catalyst according to the present invention can produce an oxide catalyst that eliminates the need of introducing complicated steps and changing facilities and can offer a high yield of unsaturated nitrile.

DESCRIPTION OF EMBODIMENTS

Hereinafter, a mode for carrying out the present invention (hereinafter, simply referred to as the "present embodiment") will be described in detail. The present embodiment described below is given for illustrating the present invention and is not intended to limit the present invention to the contents described below. The present invention can be carried out by appropriately making changes or modifications without departing from the spirit of the present invention.

[Method for Producing Oxide Catalyst]

The method for producing an oxide catalyst according to the present embodiment is a method for producing an oxide catalyst comprising Mo, V, Sb, and Nb for use in the gas-phase catalytic oxidation reaction or gas-phase catalytic ammoxidation reaction of propane or isobutane, the method comprising: a preparation step of preparing a first aqueous mixed solution containing Mo, V, and Sb (hereinafter, referred to as an "aqueous mixed solution (A)") (hereinafter, this step is also referred to as "step (a)"); a mixing step of mixing the first aqueous mixed solution with a support raw material comprising silica sol, and a Nb raw material to obtain a second aqueous mixed solution (hereinafter, referred to as an "aqueous mixed solution (B)") (hereinafter, this step is also referred to as "step (b)"); a drying step of drying the second aqueous mixed solution to obtain a dry powder (hereinafter, this step is also referred to as "step (c)"); and a calcination step of calcining the dry powder to obtain the oxide catalyst (hereinafter, this step is also referred to as "step (d)"). The support raw material comprises 25% by mass or more, based on $SiO_2$, of the silica sol having an average primary particle size of 3.0 nm or larger and smaller than 11 nm based on the total amount of the support raw material, and the silica sol comprises 55% or more of silica sol particles having a primary particle size of smaller than 11 nm. The method for producing an oxide catalyst may further comprise a removal step of removing projections present on the particle surface of the oxide catalyst (hereinafter, this step is also referred to as "step (e)"). The method for producing an oxide catalyst according to the present embodiment can produce an oxide catalyst that eliminates the need of introducing complicated steps and changing facilities and can offer a high yield of unsaturated nitrile. In this context, the "high yield" means that a higher yield is obtained using at least an oxide catalyst having the same or similar composition as the composition represented by the formula (1) mentioned later.

[Step (a): Preparation Step]

The step (a) of the present embodiment is the step of preparing an aqueous mixed solution (A) containing Mo, V, and Sb. Examples of the preparation method include, but are not limited to, a method of preparing the aqueous mixed solution (A) by mixing a raw material containing Mo (hereinafter, also referred to as a "Mo raw material"), a raw material containing V (hereinafter, also referred to as a "V raw material"), and a raw material containing Sb (hereinafter, also referred to as a "Sb raw material"). The method for the mixing described above is not particularly limited, and a mixing method known in the art can be used.

Examples of the Mo raw material include, but are not limited to, ammonium heptamolybdate [$(NH_4)_6Mo_7O_{24} \cdot 4H_2O$], molybdenum trioxide [$MoO_3$], phosphomolybdic acid [$H_3PMo_{12}O_{40}$], silicomolybdic acid [$H_4SiMo_{12}O_{40}$], and molybdenum pentoxide [$MoCl_5$]. Among them, ammonium heptamolybdate [$(NH_4)_6Mo_7O_{24} \cdot 4H_2O$] is preferred.

Examples of the V raw material include, but are not limited to, ammonium metavanadate [$NH_4VO_3$], vanadium pentoxide [$V_2O_5$], and vanadium chloride [$VCl_4$ and $VCl_3$]. Among them, ammonium metavanadate [$NH_4VO_3$] is preferred.

Examples of the Sb raw material include, but are not limited to, antimony oxide [$Sb_2O_3$ and $Sb_2O_5$], antimonious acid [$HSbO_2$], antimonic acid [$HSbO_3$], ammonium antimonate [$(NH_4)SbO_3$], antimony chloride [$Sb_2Cl_3$], organic acid salts such as tartrate of antimony, and metal antimony. Among them, diantimony trioxide [$Sb_2O_3$] is preferred.

[Step (b): Mixing Step]

In the step (b) of the present embodiment, the aqueous mixed solution (A) is mixed with a support raw material comprising silica sol, and a Nb raw material to obtain an aqueous mixed solution (B). The mixing method is not particularly limited, and a mixing method known in the art can be used. The support raw material is a raw material serving as a support in the oxide catalyst, and the Nb raw material is a raw material containing Nb.

The support raw material of the present embodiment comprises silica sol. The silica sol comprises 25% by mass or more, based on $SiO_2$, of the silica sol having an average primary particle size (hereinafter, also referred to as "average primary particle size dZ" or simply as "dZ") of 3.0 nm or larger and smaller than 11 nm (hereinafter, this silica sol is also referred to as "specific silica sol") based on the total amount (100% by mass) of the support raw material, and preferably comprises 30% by mass or more and 70% by mass or less thereof, more preferably 40% by mass or more and 60% by mass or less thereof. The average primary particle size of the silica sol is more preferably 4.0 nm or larger and smaller than 10 nm, further preferably 5.0 nm or larger and smaller than 10 nm. Examples of the silica sol include acidic sol and basic sol. Any of these silica sols can be used. Basic sol is more preferred. The silica sol having an average primary particle size in the range described above can be obtained by appropriate selection and combination from among commercially available silica sols. In the case of decreasing the average primary particle size of commercially available silica sol for use, the silica sol particles can be highly dispersed by the appropriate addition of ammonia ($NH_3$) immediately before use of the commercially available silica sol.

The surface area of the support is increased by comprising the predetermined amount or more of the silica sol having an average primary particle size of smaller than 11 nm. Presumably, this suppresses the growth of crystals of metal oxide having activity so that the crystallite size thereof is small to thereby increase the surface area of an active plane (basal plane of the crystals) contributing to reaction while decreasing the surface area of the lateral face of the crystals contributing to product decomposition, resulting in improvement in yield (however, the factor is not limited thereto). On the other hand, when the support raw material comprising the predetermined amount or more of the silica sol having an average primary particle size of 3.0 nm or larger is prepared into metal oxide slurry mentioned later, the slurry is not thickened and is free from deterioration in particle shape caused by pipe clogging. Furthermore, the specific surface area of the oxide catalyst after calcination is not too large. Therefore, adverse effects such as product decomposition of silica itself are suppressed, and the performance of the oxide catalyst is not deteriorated. Calcination at a high temperature merely intended to decrease the specific surface area of a catalyst tends to deteriorate crystals themselves of an active species.

When the support raw material comprising 70% by mass or less of the silica sol having an average primary particle size of 3.0 nm or larger is prepared into metal oxide slurry mentioned later, the slurry tends to be not thickened and be free from pipe clogging or poor moldability. Furthermore, the specific surface area of the catalyst after calcination is not too large. Therefore, adverse effects such as product decomposition of silica itself are suppressed, and the performance of the oxide catalyst is not deteriorated. Also, the amount of metal oxide is not increased too much with respect to the silica sol by comprising 30% by mass or more of the silica sol having an average primary particle size of 3.0 nm or larger. Presumably, the growth of crystals of the silica sol having activity is therefore suppressed so that the crystallite size thereof is small.

The support raw material of the present embodiment comprises 25% by mass or more, based on $SiO_2$, of the silica sol having an average primary particle size of 3.0 nm or larger and smaller than 11.0 nm based on the total amount (100% by mass) of the support raw material, and the silica sol comprises 55% or more of silica sol particles having a primary particle size of smaller than 11 nm. The content of the silica sol having a primary particle size of smaller than 11 nm is 55% or more, whereby the proportion of silica sol particles having a small primary particle size in the whole silica sol is increased. Presumably, this suppresses the growth of crystals of metal oxide having activity so that the crystallite size thereof is small to thereby increase the surface area of an active plane (basal plane of the crystals) contributing to reaction while decreasing the surface area of the lateral face of the crystals contributing to product decomposition, resulting in improvement in yield (however, the factor is not limited thereto). The content of the silica sol having a primary particle size of smaller than 11 nm is preferably less than 98% by mass, more preferably less than 96% by mass. The content of the silica sol is less than 98% by mass, whereby particularly when the support raw material is prepared into metal oxide slurry mentioned later, the slurry tends to be not thickened and be free from deterioration in particle shape caused by pipe clogging. Furthermore, the specific surface area of the oxide catalyst after calcination is not too large. Therefore, there is a tendency in which product decomposition or the like by the silica sol itself is suppressed, and the performance of the oxide catalyst is excellent.

The support raw material preferably comprises 30% by mass or more, more preferably 30% by mass or more and 70% by mass or less, further preferably 40% by mass or more and 60% by mass or less, based on $SiO_2$, of the silica sol based on the total amount (100% by mass) of the support raw material. In addition, the silica sol preferably comprises 50% by mass or more and 100% by mass or less, more preferably 65% by mass or more and 100% by mass or less, based on $SiO_2$, of the specific silica sol based on the total amount (100% by mass) of the silica sol.

The silica sol of the present embodiment may contain an alkali metal. The concentration of the alkali metal contained in the silica sol is preferably 0.0 ppm by mass or higher and 200 ppm by mass or lower. The alkali metal may be contained as impurities in the silica sol. When the concentration of the alkali metal falls within the range described above, the performance of the oxide catalyst tends to be improved. The silica sol may also contain various impurities such as nitric acid, sulfuric acid, and ammonia. The total concentration of these impurities is also preferably 0.0% by mass or more and 1.0% by mass or less from the same viewpoint as in the alkali metal. Silica sol having a small average primary particle size and having a low concentration of these impurities has been developed in recent years. Such silica sol has an impurity concentration in the range described above.

The metal composition of the oxide catalyst largely correlates with the amount of the support contained in the oxide catalyst. When the metal composition responds to each amount of the support, the performance of the oxide catalyst is remarkably improved. Accordingly, the amount of the support contained in the oxide catalyst is not too large, whereby the surface area of the support in the oxide catalyst is not too small. This tends to suppress deterioration in the dispersibility of metal oxide, which is an active species of the catalyst, after calcination and suppress deterioration in the performance of the oxide catalyst. Accordingly, the silica sol having an average primary particle size of 3.0 nm or larger is contained in the predetermined range of an amount, whereby the surface area of the catalyst is not increased too much during calcination, and silica is prevented from being incorporated into a metal component (active species) through the decomposition of the support raw material. As a result, deterioration in the performance of the oxide catalyst is suppressed. Also, the range of primary particle size distribution of this silica sol is preferably narrow. More preferably, the silica sol is monodispersed.

The size of primary particles (primary particle size) of the silica sol may be measured by particle size distribution, small-angle X-ray scattering, TEM, or the like. Among them, TEM which permits the observation of both the state and distribution of particles is preferred for the measurement. In the TEM measurement, 3 or more fields of view are randomly photographed, and the measurement values of particle diameters of 100 or more particles can be averaged and used as the average primary particle size of the silica sol. Commercially available analytical software can be appropriately used for measuring the particle diameters of 100 or more particles from images.

In the step (b) (mixing step), the support raw material preferably further comprises powder silica. This powder silica partly constitutes a silica raw material, together with the silica sol. The average primary particle size of the powder silica (hereinafter, also referred to as "average primary particle size dA of the powder silica" or simply as "dA") in the mixing step is preferably 3.0 nm or larger and smaller than 100 nm, more preferably 3.0 nm or larger and smaller than 40 nm, further preferably 3.0 nm or larger and smaller than 20 nm. The average primary particle size of the powder silica is smaller than 100 nm, whereby deterioration in the abrasion resistance of the oxide catalyst tends to be suppressed. More preferably, the average primary particle size dZ of the silica sol is 3.0 nm or larger and smaller than 11 nm, and the average primary particle size dA of the powder silica is 3.0 nm or larger and smaller than 20 nm. On the other hand, the average primary particle size of the powder silica is 3.0 nm or larger, whereby silica is presumably prevented from being incorporated into the structures of crystals (active species) through the decomposition of the support raw material during calcination. Thus, deterioration in the performance of the oxide catalyst tends to be suppressed. The powder silica having an average primary particle size in the range described above can be obtained by appropriate selection and combination from among commercially available powder silicas. The average primary particle size dA of the powder silica may be measured by particle size distribution, small-angle X-ray scattering, TEM, or the like. In the TEM measurement, 3 or more fields of view are randomly photographed, and the measurement values of particle diameters of 100 or more particles can be averaged and used as the average primary particle size of the powder silica. Commercially available analytical software can be appropriately used for measuring the particle diameters of 100 or more particles from images.

In addition to silica such as the silica sol and the powder silica, examples of the support raw material include aluminum oxide, titanium oxide, and zirconium oxide. One support raw material may be used alone, or two or more support raw materials may be used in combination. Silica is preferred for the support raw material.

In the step (b), the amount, based on $SiO_2$, of the silica sol is preferably 30% by mass or more and 70% by mass or less, more preferably 40% by mass or more and 60% by mass or less, further preferably 45% by mass or more and 55% by mass or less, based on the total amount (100% by mass) of the silica sol and the powder silica. The amount of the silica sol is 30% by mass or more, whereby deterioration in the abrasion resistance of the oxide catalyst tends to be suppressed. The amount of the silica sol is 70% by mass or less, whereby deterioration in the performance of the oxide catalyst tends to be suppressed.

Examples of the Nb raw material include, but are not limited to, niobic acid, inorganic acid salts of niobium, and organic acid salts of niobium. Among them, niobic acid is preferred. The niobic acid is represented by the formula $Nb_2O_5 \cdot nH_2O$ and is also called niobium hydroxide or niobium oxide compound.

The Nb raw material preferably contains water. In this context, the ratio between water and Nb (Nb (mol)/water (kg)) contained is more preferably 0.1 or more and 10 or less, further preferably 0.3 or more and 5.0 or less, from the viewpoint of, for example, stabilizing the Nb raw material. Also, the Nb raw material may contain an organic acid salt or a free organic acid. The organic acid is not particularly limited and is preferably oxalic acid. The molar ratio of the organic acid to niobium (organic acid/niobium) in the Nb raw material is preferably 1.0 or more and 4.0 or less.

The method for allowing the Nb raw material to contain water and the organic acid is not particularly limited, and water and the organic acid may be mixed in any order. The mixing described above may be performed at any temperature as long as the temperature is equal to or higher than a temperature at which the Nb raw material containing water does not coagulate, and is equal to or lower than a temperature at which the Nb raw material containing water does not boil. However, the mixing is preferably performed at room temperature from the viewpoint of, for example, the operability of the mixing.

The Nb raw material containing water preferably further contains hydrogen peroxide water. In this context, the molar ratio of Nb to $H_2O_2$ ($Nb/H_2O_2$) contained in the Nb raw material is preferably 0.5 or more and 20 or less, more preferably 1.0 or more and 10 or less, further preferably 1.0 or more and 5.0 or less, from the viewpoint of, for example, stabilizing the Nb raw material in a dissolved state by the formation of a complex, properly adjusting the redox state of elements constituting the oxide catalyst, and achieving the proper catalyst performance of the resulting oxide catalyst.

In the step (a) and/or the step (b), a raw material containing at least one element selected from the group consisting of W, La, Ce, Yb, and Y (hereinafter, also referred to as "component Z") (hereinafter, this raw material is also referred to as a "Z raw material") may be further mixed. The Z raw material is any substance containing the component Z. Examples thereof include, but are not limited to, a compound containing the component Z, and the component Z whose metal has been solubilized with an appropriate reagent. Examples of the compound containing the component Z include, but are not limited to, ammonium salt, nitrate, carboxylate, carboxylic acid ammonium salt, peroxocarboxylate, peroxocarboxylic acid ammonium salt, halogenated ammonium salt, halide, acetyl acetonate, and alkoxide. Among them, a water-soluble raw material such as nitrate or carboxylate is preferred.

In the step (a) and/or the step (b), it is preferred to adjust a raw material ratio such that the oxide catalyst to be obtained by the step (d) has the composition represented by the formula (1) given below. Use of the oxide catalyst having the composition represented by the following formula (1) tends to further improve the yield of unsaturated nitrile.

$$MoV_aSb_bNb_cZ_dO_n \qquad (1)$$

wherein Z represents at least one element selected from the group consisting of W, La, Ce, Yb, and Y; a, b, c, and d represent values in the ranges of $0.01 \leq a \leq 0.35$, $0.01 \leq b \leq 0.35$, $0.01 \leq c \leq 0.20$, and $0.00 \leq d \leq 0.10$, respectively; and n represents a value that satisfies the balance among the valences.

In the formula (1), (a/b) is preferably 0.50 or more and 0.98 or less, more preferably 0.60 or more and 0.97 or less, further preferably 0.65 or more and 0.96 or less. (a/b) is 0.98 or less, whereby in the case of using silica sol having a small particle size, presumably, Sb is highly dispersed easily in the silica support so that active crystals are formed in a highly dispersed state. Thus, the catalyst tends to be obtained at a high yield. Furthermore, Mo and Sb form a complex oxide having a low melting point during calcination. This can presumably prevent the surface area from being too large even when silica sol having a small particle size is used.

The composition of the oxide catalyst obtained after the step (d) may be different from the composition of the finally obtained oxide catalyst. Specifically, this is because the composition of projections of the oxide catalyst mentioned later is different from the composition of the main body of the oxide catalyst, and the composition of the oxide catalyst is changed between before and after the step (e) of removing the projections. In the step (a) and/or the step (b), a composition ratio may be set by also taking the change in consideration. In the present specification, the "projection" refers to matter effused and/or attached to the surface of a calcined form obtained by final calcination mentioned later, or matter projected and/or attached from the surface of the calcined form.

Hereinafter, the step (a) and/or the step (b) will be described by taking, as an example, the case of using water as a solvent and/or a dispersion medium and preparing an aqueous mixed solution (B) containing the Mo raw material, the V raw material, the Sb raw material, the Nb raw material, and the Z raw material. However, the step (a) and/or the step (b) is not limited thereto.

In the step (a), the Mo raw material, the V raw material, the Sb raw material, and the Z raw material are added to water, and the mixture can be heated to prepare an aqueous mixed solution (A). For the preparation of the aqueous mixed solution (A), it is preferred to adjust a heating temperature and a heating time such that each raw material can be sufficiently dissolved. Specifically, the heating temperature is preferably 70° C. or higher and 100° C. or lower, and the heating time is preferably 30 minutes or longer and 5 hours or shorter. In this operation, it is preferred to stir the aqueous mixed solution (A) such that the raw materials are easily dissolved. In this operation, the atmosphere in which the aqueous mixed solution (A) is prepared may be an air atmosphere. Alternatively, a nitrogen atmosphere may be used from the viewpoint of adjusting the oxidation number of the resulting oxide catalyst. The state of the aqueous mixed solution (A) after the completion of the heating described above is also referred to as an aqueous mixed solution (A'). The temperature of the aqueous mixed solution (A') is preferably kept at 20° C. or higher and 80° C. or lower, more preferably 40° C. or higher and 80° C. or lower. The temperature of the aqueous mixed solution (A') is 20° C. or higher, whereby the metal species dissolved in the aqueous mixed solution (A') are less likely to be deposited.

Subsequently, the support raw material comprising silica sol can be added to the aqueous mixed solution (A) or the aqueous mixed solution (A'). Among them, it is preferred to add the silica sol to the aqueous mixed solution (A'). The silica sol functions as a support in the formed oxide catalyst. The temperature at which the silica sol is added is preferably 80° C. or lower. In the case of adding the silica sol at 80° C. or lower, the silica sol tends to have relatively high stability and prevent the gelation of the aqueous mixed solution (B). The time when the silica sol is added may be at the start of aging mentioned later, may be during aging, or may be immediately before drying of the aqueous mixed solution (B).

Furthermore, it is preferred to add an appropriate amount of hydrogen peroxide water to the aqueous mixed solution (A) or the aqueous mixed solution (A') according to the need, from the viewpoint of adjusting the oxidation number of a complex oxide in the resulting oxide catalyst. The time when the hydrogen peroxide water is added may be addition to the aqueous mixed solution (A) or the aqueous mixed solution (A') itself or addition during the preparation of the aqueous mixed solution (A) or the aqueous mixed solution (A'), and may be before or after the addition of the silica sol. In this operation, the amount of the hydrogen peroxide water added is preferably 0.01 or more and 5.0 or less, more preferably 0.5 or more and 3.0 or less, further preferably 1.0 or more and 2.5 or less, in terms of the molar ratio of the hydrogen peroxide water to Sb ($H_2O_2/Sb$), from the viewpoint of adjusting the oxidation number of the resulting oxide catalyst to within a proper range.

It is preferred to adjust a heating temperature and a heating time after the addition of the hydrogen peroxide water to the aqueous mixed solution (A) or the aqueous mixed solution (A') such that liquid-phase oxidation reaction by the hydrogen peroxide water can proceed sufficiently. Specifically, the heating temperature is preferably 20° C. or higher and 80° C. or lower, and the heating time is preferably 5 minutes or longer and 4 hours or shorter. Likewise, the number of rotations of stirring during the heating can be adjusted to the moderate number of rotations that accelerates liquid-phase oxidation reaction by the hydrogen peroxide water. It is preferred to keep the stirred state during the heating, from the viewpoint that liquid-phase oxidation reaction by the hydrogen peroxide water proceeds sufficiently. The aqueous mixed solution thus prepared by the addition of the hydrogen peroxide water is also referred to as an aqueous mixed solution (A").

Next, the Nb raw material is preferably prepared into a mixed solution ($B_0$) by heating and stirring the Nb raw material and dicarboxylic acid in water. Examples of the dicarboxylic acid include, but are not limited to, oxalic acid [$(COOH)_2$]. Subsequently, hydrogen peroxide water is preferably added to the mixed solution ($B_0$) to prepare an aqueous mixed solution ($B_1$). In this operation, the molar ratio of the hydrogen peroxide water to Nb ($H_2O_2/Nb$) is preferably 0.5 or more and 20 or less, more preferably 1.0 or more and 10 or less, further preferably 1.0 or more and 5.0 or less, from the viewpoint of, for example, stabilizing the Nb raw material in a dissolved state by the formation of a complex, properly adjusting the redox state of elements constituting the oxide catalyst, and achieving the proper catalyst performance of the resulting oxide catalyst.

Subsequently, the aqueous mixed solution (A), the aqueous mixed solution (A'), or the aqueous mixed solution (A") and the aqueous mixed solution ($B_0$) or the aqueous mixed solution ($B_1$) can be mixed according to the intended composition to obtain an aqueous mixed solution (B). In this operation, a W raw material or powder silica may be further mixed therewith.

Alternatively, the aqueous mixed solution ($B_0$) or the aqueous mixed solution ($B_1$) may be mixed with a silica raw material in advance. The order in which the aqueous mixed solution ($B_0$) or the aqueous mixed solution ($B_1$) and the silica raw material are mixed is not particularly limited. The silica raw material may be added to the aqueous mixed solution ($B_0$) or the aqueous mixed solution ($B_1$), or the aqueous mixed solution ($B_0$) or the aqueous mixed solution ($B_1$) may be added to the silica raw material. Among them, it is more preferred to add the silica raw material to the aqueous mixed solution ($B_0$) or the aqueous mixed solution ($B_1$), from the viewpoint of suppressing the deposition of Nb in the aqueous mixed solution ($B_0$) or the aqueous mixed solution ($B_1$). After the addition, the mixture may be left standing or may be stirred, and may be further sonicated using a homogenizer or the like. In this operation, a portion of other metal raw materials may be added to the aqueous mixed solution ($B_0$) or the aqueous mixed solution ($B_1$) in advance, or a portion of other metal raw materials may be added to the silica raw material in advance. The other metal raw materials refer to the Mo raw material, the V raw material, the Sb raw material, W raw material, and the Z raw material. In this case, the amount of the other metal raw materials added is preferably less than 50% by mass, more preferably 0.0% by mass or more and 40% by mass or less, further preferably 0.0% by mass or more and 30% by mass or less, based on the total amount of the metal raw materials to be finally added.

It is preferred to add the powder silica to the "aqueous mixed solution (A")" or a "solution obtained by mixing the aqueous mixed solution (B) with the W raw material", from the viewpoint of achieving the proper catalyst performance. Although the powder silica may be added as it is, it is more preferred to add a liquid containing the powder silica dispersed in water, i.e., a powder silica-containing suspension. In this context, the powder silica concentration in the powder silica-containing suspension is preferably 1.0% by mass or higher and 30% by mass or lower, more preferably 3.0% by mass or higher and 20% by mass or lower. The powder silica concentration is 1.0% by mass or higher, whereby the catalyst particles tend to be able to be prevented from having a distorted shape due to the low viscosity of the aqueous mixed solution (B). The catalyst particles also tend to be able to be prevented from being recessed, for example. The powder silica concentration is 30% by mass or lower, whereby the gelation of the aqueous mixed solution (B) and pipe clogging attributed to the large viscosity of the aqueous mixed solution (B) tend to be able to be avoided. Also, a dry powder tends to be able to be easily obtained. Furthermore, the performance of the oxide catalyst tends to be further improved.

The obtained aqueous mixed solution (B) may be subjected to aging treatment. The aging of the aqueous mixed solution (B) means that the aqueous mixed solution (B) is left standing or stirred for a predetermined time. The aging time is preferably 90 minutes or longer and 50 hours or shorter, more preferably 90 minutes or longer and 6 hours or shorter. The range described above tends to facilitate forming the aqueous mixed solution (B) having a suitable redox state (potential) and further improve the catalyst performance of the resulting complex oxide.

In this context, in the case of industrially producing the oxide catalyst through drying using a spray dryer, the processing speed of the spray dryer usually becomes rate-controlling so that the completion of the spray drying of the whole mixed solution tends to be time-consuming after partial spray drying of the aqueous mixed solution (B). In the meantime, the aging of a non-spray-dried aqueous mixed solution is continued. Thus, the aging time includes not only an aging time before drying in the step (c) mentioned later but a time from the start of drying to the completion thereof.

The aging temperature is preferably 25° C. or higher from the viewpoint of preventing the condensation of a Mo component or the deposition of metal oxide by V and other metal species or a plurality of metals. Also, the aging temperature is preferably 65° C. or lower from the viewpoint of forming the aqueous mixed solution (B) in a preferred form by preventing a complex containing Nb and hydrogen peroxide from being hydrolyzed too much. The aging temperature is preferably 25° C. or higher and 65° C. or lower, more preferably 45° C. or higher and 60° C. or lower, from these viewpoints. The catalyst can be further reduced during calcination by extending the aging time and elevating the aging temperature, for example, or combining these operations.

The diligent studies of the present inventors have revealed that the rate of reduction of the catalyst after calcination has given correlation with the redox potential of the aqueous mixed solution (B). The catalyst after calcination is more likely to be oxidized with increase in the redox potential of the aqueous mixed solution (B) and is more likely to be reduced with decrease therein. Therefore, the redox potential of the aqueous mixed solution (B) is preferably 400 mV or higher and 600 mV or lower, more preferably 420 mV or higher and 520 mV or lower, further preferably 420 mV or higher and 500 mV or lower. The redox potential of the aqueous mixed solution (B) can be measured by using a commercially available electrometer, though the measurement is not particularly limited thereto. Specifically, the redox potential is measured by a method described in Examples mentioned later.

[Step (c): Drying Step]

The step (c) of the present embodiment is the step of drying the aqueous mixed solution (B) to obtain a dry powder. The drying can be performed by a method known in the art and can be performed by, for example, spray drying or evaporation to dryness. In the case of adopting a fluidized-bed reaction system in gas-phase catalytic oxidation reaction or gas-phase catalytic ammoxidation reaction using the oxide catalyst, it is preferred to obtain a dry powder in a microsphere form in the step (c), from the viewpoint of, for example, achieving preferred flowability in a reactor. It is preferred to adopt spray drying from the viewpoint of obtaining a dry powder in a microsphere form. Spraying in the spray drying method may be performed by a centrifugation system, a two-fluid nozzle system, or a high-pressure nozzle system. Steam, or air heated using an electric heater or the like can be used as a dry heat source.

It is preferred to adjust a spraying rate, the feeding rate of the aqueous mixed solution (B), the number of rotations of an atomizer for a centrifugation system, or the like such that the resulting dry powder has a suitable size. The average particle size of the dry powder is preferably 35 µm or larger and 75 µm or smaller, more preferably 40 µm or larger and 70 µm or smaller, further preferably 45 µm or larger and 65 µm or smaller. The average particle size is not largely changed after calcination. Examples of the method for adjusting the average particle size of the dry powder include a classification method described in Examples.

[Step (d): Calcination Step]

The step (d) of the present embodiment is the step of calcining the dry powder to obtain the oxide catalyst. For example, a rotary kiln can be used as a calcination apparatus for calcining the dry powder. The shape of a calciner in which the dry powder is calcined is not particularly limited. A tube shape (calcination tube) is preferred from the viewpoint that continuous calcination can be carried out. A cylindrical shape is more preferred. The heating system is preferably an external heating system from the viewpoint of, for example, facilitating adjusting the calcination temperature to a preferred temperature elevation pattern. An electric furnace can be suitably used as an external heat source. The size, material, or the like of the calcination tube can be appropriately selected according to calcination conditions and the amount of the oxide catalyst produced.

In the step (d), it is desirable to perform calcination in two divided portions. When the first calcination is used as pre-stage calcination and the later calcination is used as final calcination, it is preferred to perform the pre-stage calcination in the temperature range of 250° C. or higher and 400° C. or lower and perform the final calcination in the temperature range of 450° C. or higher and 700° C. or lower. The pre-stage calcination and the final calcination may be continuously carried out, or the pre-stage calcination may be temporarily terminated and then the final calcination may be carried out anew. Also, the pre-stage calcination and the final calcination may each be divided into several stages.

The calcination atmosphere may be an air atmosphere or may be circulated air. It is preferred to carry out at least a portion of the calcination while circulating an inert gas such as nitrogen substantially free from oxygen, from the viewpoint of preferably adjusting the redox state. In the case of performing the calcination in a batch system, the amount of the inert gas supplied is preferably 50 NL/hr or larger, more preferably 50 NL/hr or larger and 5000 NL/hr or smaller, further preferably 50 NL/hr or larger and 3000 NL/hr or smaller, per kg of the dry powder from the viewpoint of preferably adjusting the redox state. In this context, the unit "NL" means the volume of a gas measured under standard temperature and pressure conditions, i.e., at 0° C. and 1 atm.

The rate of reduction of a calcined form after the pre-stage calcination (preliminarily calcined form) is preferably 7.0% or higher and 15% or lower, more preferably 8.0% or higher and 12% or lower, further preferably 9.0% or higher and 12% or lower. When the rate of reduction falls within this range, there is a tendency in which the activity of the oxide catalyst is further improved, and catalyst production efficiency is further improved. Examples of the method for controlling the rate of reduction in the desired range include, but are not limited to, a method of changing the pre-stage calcination temperature, a method of adding an oxidizing component such as oxygen into the calcination atmosphere, and a method of adding a reducing component into the calcination atmosphere. These methods may be combined. The rate of reduction of a catalyst precursor is represented by the following expression (1):

$$\text{Rate of reduction (\%)} = ((n_0 - n)/n_0) \times 100 \tag{1}$$

wherein n is the number of oxygen atoms that satisfies the valences of elements, except for oxygen, constituting the catalyst precursor, and $n_0$ is the number of oxygen atoms required for the elements, except for oxygen, constituting the catalyst precursor to have their respective highest oxidation numbers.

In order to determine the rate of reduction, the value of $(n_0-n)$ in the expression (1) is obtained by the redox titration of a sample with $KMnO_4$. One example of the measurement method will be given below.

Approximately 200 mg of the sample is precisely weighed into a beaker. An excessive amount of an aqueous $KMnO_4$ solution having a known concentration is further added thereto. 150 mL of purified water and 2 mL of 1:1 sulfuric acid (i.e., an aqueous sulfuric acid solution obtained by mixing concentrated sulfuric acid and purified water at a volume ratio of 1/1) are further added thereto. Then, the beaker is covered with watch glass and stirred for 1 hour in a hot water bath of 70° C.±2° C. to oxidize the sample. Since an excess of $KMnO_4$ is present and unreacted $KMnO_4$ is present in the solution, it is confirmed that the color of the solution is purple. After the completion of the oxidation, the solution is filtered through filter paper, and the whole amount of the filtrate is recovered. An aqueous sodium oxalate solution having a known concentration is added in excessive amount with respect to $KMnO_4$ present in the filtrate, and the solution is heated to a temperature of 70° C. and stirred. After confirmation that the liquid becomes clear and colorless, 2 mL of 1:1 sulfuric acid is added thereto. While the temperature of the solution is kept at 70° C.±2° C., the solution is continuously stirred and titrated with an aqueous $KMnO_4$ solution having a known concentration. The end point is set to when the light pink color of the solution continues for approximately 30 seconds by $KMnO_4$. The amount of $KMnO_4$ consumed by the oxidation of the sample is determined from the total amount of $KMnO_4$ and the total amount of $Na_2C_2O_4$. $(n_0-n)$ is calculated from this value, and the rate of reduction is determined on the basis thereof.

[Step (e): Removal Step]

The step (e) of the present embodiment is the step of removing projections present on the particle surface of the oxide catalyst. The projections are mostly protruded crystals of oxide or other impurities. Particularly, in the case of a calcined form containing a plurality of metals, oxide differing in composition from crystals constituting the most part of the calcined form may be formed in a form effused from the main body of the calcined form. Such projections tend to be responsible for reduction in flowability. Therefore, the performance of the oxide catalyst tends to be enhanced by removing the projections from the surface of the oxide catalyst. In the case of removing the projections on a gram scale, the following apparatus may be used: a vertical tube provided with a perforated board having one or more holes at the bottom and paper filter in the upper part can be used. The calcined form is added to this vertical tube, and air is circulated from underneath so that air flow is created from each hole and thereby promotes the contact between the particles of the calcined form to remove the projections.

[Oxide Catalyst]

The oxide catalyst of the present embodiment is obtained by the aforementioned method for producing an oxide catalyst. The obtained oxide catalyst preferably has the composition represented by the following formula (1):

$$MoV_aSb_bNb_cZ_dO_n \tag{1}$$

wherein Z represents at least one element selected from the group consisting of W, La, Ce, Yb, and Y; a, b, c, and d represent values in the ranges of $0.01 \le a \le 0.35$, $0.01 \le b \le 0.35$, $0.01 \le c \le 0.20$, and $0.00 \le d \le 0.10$, respectively; and n represents a value that satisfies the balance among the valences. The composition of the oxide catalyst can be measured by fluorescence X-ray analysis (trade name "RIX1000" manufactured by Rigaku Corp., Cr tube, tube voltage: 50 kV, tube current: 50 mA).

The oxide catalyst preferably comprises 30% by mass or more and 70% by mass or less of the support based on the total amount (100% by mass) of the oxide catalyst. In order to obtain the oxide catalyst having such a range, the oxide catalyst preferably comprises 30% by mass or more and 70% by mass or less, based on $SiO_2$, of the silica (silica sol and powder silica). The silica can be used at more preferably 40% by mass or more and 60% by mass or less, further preferably 45% by mass or more and 55% by mass or less. The strength of the oxide catalyst comprising 30% by mass or more of the support tends to be further improved. The oxide catalyst comprising 70% by mass or less of the support tends to have higher activity.

The content of the support in the oxide catalyst is determined by measurement by fluorescence X-ray analysis (trade name "RIX1000" manufactured by Rigaku Corp., Cr tube, tube voltage: 50 kV, tube current: 50 mA).

[Method for Producing Unsaturated Nitrile]

The method for producing unsaturated nitrile according to the present embodiment comprises a production step of producing unsaturated nitrile by the gas-phase catalytic oxidation reaction or gas-phase catalytic ammoxidation reaction of propane or isobutane in the presence of an oxide catalyst produced by the method for producing an oxide catalyst according to the present embodiment. The production step is preferably the step of producing unsaturated nitrile by the gas-phase catalytic ammoxidation reaction of propane or isobutane. Hereinafter, the method for producing acrylonitrile as the unsaturated nitrile using the oxide catalyst of the present embodiment packed in a reactor will be described.

<Gas-Phase Catalytic Oxidation Reaction or Gas-Phase Catalytic Ammoxidation Reaction>

Propane or isobutane and oxygen are used in the gas-phase catalytic oxidation reaction, and propane or isobutane, ammonia, and oxygen are used in the gas-phase catalytic ammoxidation reaction. Among them, propane and ammonia are not necessarily required to be highly pure, and may be industrial-grade gasses such as propane containing 3% by volume or less of impurities such as ethane, ethylene, n-butane, and isobutane, and ammonia containing 3% by volume or less of impurities such as water. Examples of the oxygen include, but are not limited to, air, oxygen-enriched air, pure oxygen, and gases obtained therefrom by dilution with an inert gas such as helium, argon, carbon dioxide, or nitrogen, or water vapor. Among them, air is preferred for use on an industrial scale because of convenience.

Examples of the reaction conditions of the gas-phase catalytic oxidation reaction include, but are not particularly limited to, conditions given below. The molar ratio of oxygen to propane or isobutane (oxygen/(propane or isobutane)) supplied to the reaction is preferably 0.1 or more and 6.0 or less, more preferably 0.5 or more and 4.0 or less. The reaction temperature is preferably 300° C. or higher and 500° C. or lower, more preferably 350° C. or higher and 500° C. or lower. The reaction pressure is preferably $5.0 \times 10^4$ Pa or higher and $5.0 \times 10^5$ Pa or lower, more preferably $1.0 \times 10^5$ Pa or higher and $3.0 \times 10^5$ Pa or lower. The contact time is preferably 0.1 sec·g/cm$^3$ or longer and 10 sec·g/cm$^3$ or shorter, more preferably 0.5 sec·g/cm$^3$ or longer and 5.0 sec·g/cm$^3$ or shorter. The range described above tends to be able to further suppress the formation of by-products and further improve the yield of the unsaturated nitrile.

In the present embodiment, the contact time is defined according to the following expression:

Contact time (sec·g/cm$^3$)=($W/F$)×273/(273+$T$)

In this context, W, F, and T are defined as follows.
W=amount of the catalyst packed (g)
F=flow rate (Ncm$^3$/sec) of a mixed gas of the raw materials in a standard state (0° C., $1.013 \times 10^5$ Pa)
T=reaction temperature (° C.) The rate of conversion of the alkane such as propane or isobutane, and the yield of unsaturated acid or unsaturated nitrile abide by the following definitions:

Rate of conversion of the alkane (%)=(The number of moles of the reacted alkane)/(The number of moles of the supplied alkane)×100

Yield of unsaturated acid or unsaturated nitrile (%)= (The number of moles of the formed unsaturated acid or unsaturated nitrile)/(The number of moles of the supplied alkane)×100

Examples of the reaction conditions of the gas-phase catalytic ammoxidation reaction include, but are not particularly limited to, conditions given below. The molar ratio of oxygen to propane or isobutane (oxygen/(propane or isobutane)) supplied to the reaction is preferably 0.1 or more and 6.0 or less, more preferably 0.5 or more and 4.0 or less. The molar ratio of ammonia to propane or isobutane (ammonia/(propane or isobutane)) supplied to the reaction is preferably 0.3 or more and 1.50 or less, more preferably 0.7 or more and 1.20 or less. The reaction temperature is preferably 320° C. or higher and 500° C. or lower, more preferably 370° C. or higher and 460° C. or lower. The reaction pressure is preferably $5.0 \times 10^4$ Pa or higher and $5.0 \times 10^5$ Pa or lower, more preferably $1.0 \times 10^5$ Pa or higher and $3.0 \times 10^5$ Pa or lower. The contact time is preferably 0.1 sec·g/cm$^3$ or longer and 10 sec·g/cm$^3$ or shorter, more preferably 0.5 sec·g/cm$^3$ or longer and 5.0 sec·g/cm$^3$ or shorter. The range described above tends to be able to further suppress the formation of by-products and further improve the yield of the unsaturated nitrile.

A system known in the art such as an immobilized-bed, fluidized-bed, or moving-bed system can be adopted as a reaction system in the gas-phase catalytic oxidation reaction and the gas-phase catalytic ammoxidation reaction. Among them, a fluidized-bed reactor is preferred because the heat of reaction is easily removed. The gas-phase catalytic ammoxidation reaction may be performed in a single current manner or in a recycling manner.

EXAMPLES

Hereinafter, the present embodiment will be described in more detail with reference to specific Examples and Comparative Examples. The present embodiment is not limited by Examples and Comparative Examples given below by any means without departing from the spirit of the present invention. Measurement of various physical properties, and evaluation in Examples and Comparative Examples mentioned later were performed by the following methods.

(Preparation Example) Niobium Mixed Solution

A niobium mixed solution was prepared by the following method: 10 kg of water was mixed with 1.420 kg of niobic acid containing 79.8% by mass of $Nb_2O_5$, and 5.134 kg of oxalic acid dihydrate ($H_2C_2O_4 \cdot 2H_2O$). The oxalic acid/niobium molar ratio for the preparation was 4.8, and the niobium concentration for the preparation was 0.52 mol/kg. This solution was heated and stirred at 95° C. for 2 hours to obtain a mixed solution containing niobium dissolved therein. This mixed solution was left standing and cooled in ice. Then, solid matter was filtered off by suction filtration to obtain a homogeneous niobium mixed solution. This niobium mixed solution had an oxalic acid/niobium molar ratio of 2.340 in analysis described below. The obtained niobium mixed solution was used as a niobium raw material solution ($B_0$) in the production of oxide catalysts of Examples 1 to 12 and Comparative Examples 1 to 4 described below.

(Physical Property 1) Niobium Concentration and Oxalic Acid Concentration 10 g of the niobium mixed solution obtained as described above was precisely weighed into a crucible, dried overnight at 95° C., and heat-treated at 600° C. for 1 hour to obtain 0.8125 g of $Nb_2O_5$. From this result, the niobium concentration was 0.611 mol (Nb)/kg (niobium mixed solution). Also, 3 g of this niobium mixed solution was precisely weighed into a 300-mL glass beaker. 200 mL of hot water of approximately 80° C. was added thereto, and 10 mL of 1:1 sulfuric acid was subsequently added thereto. While the temperature of the solution was kept at 70° C. on a hot stirrer, the obtained mixed solution was titrated using ¼ N $KMnO_4$ with stirring. The end point was set to when light pink color continued approximately 30 seconds or longer by $KMnO_4$. The oxalic acid concentration was determined from the titer thereof according to the following expression and was 1.430 mol (oxalic acid)/kg (niobium mixed solution):

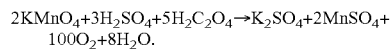

$2KMnO_4+3H_2SO_4+5H_2C_2O_4 \rightarrow K_2SO_4+2MnSO_4+ 10CO_2+8H_2O.$ (Physical Property 2) Redox Potential of Aqueous Mixed Solution ($B_1$)

The redox potential of an aqueous mixed solution ($B_1$) was measured using a commercially available electrometer (manufactured by DKK-Toa Corp.).

(Physical Property 3) Average Primary Particle Sizes of Silica Sol and Powder Silica, Content of Silica Sol Having Primary Particle Size of Smaller than 11 nm, and Silica Sol Content For each silica sol and powder silica used in Examples and Comparative Examples, in order to obtain the average primary particle sizes of the silica sol and the powder silica and the proportion of silica sol having a primary particle size of smaller than 11 nm, 3 or more fields of view were randomly photographed by use of TEM (HITACHI HT7700, acceleration voltage: 125 kV) to obtain images of 100 or more particles each of the silica sol and the powder silica. The silica sol sample used in the photographing was diluted with purified water and added dropwise to a microgrid such that the silica sol particles did not overlap with each other. The average primary particle sizes of the silica sol and the powder silica, and the proportion of the silica sol having a primary particle size of smaller than 11 nm were measured and calculated using "image analysis software A-ZO-Kun" manufactured by Asahi Kasei Engineering Corp. After startup of "image analysis software A-ZO-Kun", the images measured by TEM were scanned thereinto, and the pixel length was set in order to match the lengths in the images to actual lengths. "Round particle analysis" was executed to measure and calculate the diameters of all round (spherical) particles in the images. The settings for analysis were "bright" for particle brightness, "present" for noise removing filter, "50" for overlapping degree, "50" for circular threshold value, and "20 to 100 pixels" for measurement range. From the data on primary particle sizes and the number of particles, the primary particle size at 50% cumulative ratio of the number of particles counted from a silica sol particle having the smallest primary particle size was used as the average primary particle size. Also, the cumulative ratio of the number of particles counted up to a silica sol particle having a primary particle size of smaller than 11 nm was used as the content of the silica sol having a primary particle size of smaller than 11 nm. In Table 1, "Silica sol content" represents the content of the whole silica sol based on the total amount (100% by mass) of the support raw material.

(Physical Property 4) Composition of Oxide Catalyst

The composition of an oxide catalyst was measured by fluorescence X-ray analysis (trade name "RIX1000" manufactured by Rigaku Corp., Cr tube, tube voltage: 50 kV, tube current: 50 mA).

(Physical Property 5) Amount of Support

The amount of a support was defined as the amount of the support (% by mass) based on the total amount (100% by mass) of the oxide catalyst obtained in each of Examples and Comparative Examples mentioned later. The obtained oxide catalyst was assayed by fluorescence X-ray analysis (trade name "RIX1000" manufactured by Rigaku Corp., Cr tube, tube voltage: 50 kV, tube current: 50 mA) to determine the amount of the support.

(Evaluation) Yield of Acrylonitrile (Unsaturated Nitrile), and Rate of Conversion of Propane In Examples and Comparative Examples, the yield of acrylonitrile was determined as follows: the number of moles of formed acrylonitrile was measured by creating in advance a calibration curve by the gas chromatography (GC; product name "GC2014" manufactured by Shimadzu Corp.) analysis of acrylonitrile gas having a known concentration, and then quantitatively injecting a gas formed by ammoxidation reaction into GC. From the measured number of moles of acrylonitrile, the yield of acrylonitrile was determined according to the following expression:

Yield of acrylonitrile (%)=(The number of moles of the formed acrylonitrile)/(The number of moles of the supplied propane)×100

Also, the rate of conversion of propane was determined as follows: the number of moles of unreacted propane was measured by creating in advance a calibration curve by the GC analysis of propane gas having a known concentration, and then quantitatively injecting a gas formed by ammoxidation reaction into GC. From the measured number of moles of unreacted propane, the rate of conversion of propane was determined according to the following expression:

Rate of conversion of propane (%)=((The number of moles of the supplied propane)−(The number of moles of the unreacted propane))/(The number of moles of the supplied alkane)×100

Example 1

(Preparation Step) Aqueous Mixed Solution (A1)

475.4 g of ammonium heptamolybdate [$(NH_4)_6Mo_7O_{24} \cdot 4H_2O$], 62.6 g of ammonium metavanadate [$NH_4VO_3$], 93.7 g of diantimony trioxide [$Sb_2O_3$], and 7.1 g of cerium nitrate [$Ce(NO_3)_3 \cdot 6H_2O$] were added to 1702 g of water, and the mixture was heated at 95° C. for 1 hour with stirring to prepare an aqueous mixed solution ($A_1$).

66.7 g of hydrogen peroxide water containing 30% by mass of $H_2O_2$ was added to 481.4 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 1515.5 g of silica sol containing 21.0% by mass of $SiO_2$ and having an average primary particle size of 9.0 nm was added, further 109.1 g of hydrogen peroxide water containing 30% by mass of $H_2O_2$ was added, and the mixture was continuously stirred at 55° C. for 30 minutes. Next, the aqueous mixed solution ($A_2$), 38.3 g of an aqueous ammonium metatungstate solution (purity: 50%), and a dispersion obtained by dispersing 293.8 g of powder silica having an average primary particle size of 12 nm in 2643.8 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer (dry heat source: air; the same dry heat source thereas was used in a centrifugal spray dryer described below) and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average primary particle size of 54 μm. The particle content and the average particle size were measured using trade name "LS230" manufactured by Beckman Coulter, Inc. (a particle content and an average particle size given below were measured in the same way thereas).

(Calcination Step) Oxide Catalyst ($E_1$)

The obtained dry powder ($D_1$) was supplied in an amount of 80 g/hr to a cylindrical SUS calcination tube of continuous type having a diameter within a rotary kiln (inside diameter; the same holds true for a diameter given below) of 3 inch and a length of 89 cm. 1.5 NL/min of nitrogen gas was injected into the calcination tube both in a direction opposite to the direction of supply of the dry powder (i.e., counter current; the same holds true for an opposite direction given below), and in the same direction thereas (i.e., parallel current; the same holds true for the same direction given below). The total flow rate was set to 3.0 NL/min. While the calcination tube was rotated at a rate of 4 rpm, pre-stage calcination was performed with the temperature of the kiln set such that the temperature was elevated to the highest calcination temperature 360° C. over 4 hours and kept at 360° C. for 1 hour. The recovered preliminarily calcined form was supplied in an amount of 60 g/hr to a SUS calcination tube of continuous type having a diameter within a rotary kiln of 3 inch and a length of 89 cm. 1.1 NL/min of nitrogen gas was injected into the calcination tube both in a direction opposite to the direction of supply of the dry powder and in the same direction thereas. The total flow rate was set to 2.2 NL/min. Final calcination was performed with the temperature of the kiln set such that the temperature was able to be elevated to 680° C. in 2 hours, kept at 680° C. for 2 hours, and then lowered to 600° C. over 8 hours, to obtain an oxide catalyst ($E_1$).

(Removal Step)

50 g of the oxide catalyst ($E_1$) was added to a vertical tube (inside diameter: 41.6 mm, length: 70 cm) equipped with a perforated disc having 3 holes of 1/64 inch in diameter at the bottom and paper filter in the upper part. Subsequently, air was circulated at room temperature upward from below the vertical tube via each hole to promote the contact between the particles of the calcined form. The air flow length in the flow direction of this air flow was 56 mm, and the average linear velocity of the air flow was 332 m/s. The oxide catalyst ($E_1$) obtained 24 hours later had no projection.

(Production Step) Ammoxidation Reaction of Propane

Propane was subjected to gas-phase catalytic ammoxidation reaction by the following method using the oxide catalyst ($E_1$) obtained as described above: 38 g of the oxide catalyst was packed into a Vycor glass fluidized-bed reaction tube having an inside diameter of 25 mm, and a mixed gas having a molar ratio of propane:ammonia:oxygen:helium=1:1:2.9:18 was supplied thereto at a reaction temperature of 445° C. and a reaction pressure of 50 kPa for a contact time of 3.0 (sec·g/cm$^3$). The reaction yield of acrylonitrile (AN) when continuous reaction was performed for 10 days using this catalyst is shown in Table 1.

Examples 2 to 4

Each oxide catalyst was produced in the same way as in Example 1 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

Example 5

(Preparation Step) Aqueous Mixed Solution ($A_1$)

388.1 g of ammonium heptamolybdate [$(NH_4)_6Mo_7O_{24}\cdot 4H_2O$], 51.1 g of ammonium metavanadate [$NH_4VO_3$], 76.5 g of diantimony trioxide [$Sb_2O_3$], and 5.8 g of cerium nitrate [$Ce(NO_3)_3\cdot 6H_2O$] were added to 1381 g of water, and the mixture was heated at 95° C. for 1 hour with stirring to prepare an aqueous mixed solution ($A_1$).

54.5 g of hydrogen peroxide water containing 30% by mass of $H_2O_2$ was added to 393.0 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 1782.8 g of silica sol containing 21.0% by mass of $SiO_2$ and having a primary particle size of 9.0 nm was added, further 89.1 g of hydrogen peroxide water containing 30% by mass of $H_2O_2$ was added, and the mixture was continuously stirred at 55° C. for 30 minutes. Next, the aqueous mixed solution ($A_2$), 31.3 g of an aqueous ammonium metatungstate solution (purity: 50%), and a dispersion obtained by dispersing 345.6 g of powder silica having an average primary particle size of 12 nm in 3110.4 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average particle size of 54 μm.

The obtained dry powder ($D_1$) was subjected to the calcination step, the removal step, and the production step in the same way as in Example 1. The reaction yield of acrylonitrile (AN) is shown in Table 1.

Example 6

(Preparation Step) Aqueous Mixed Solution ($A_1$)

582.2 g of ammonium heptamolybdate [$(NH_4)_6Mo_7O_{24}\cdot 4H_2O$], 76.6 g of ammonium metavanadate [$NH_4VO_3$], 118.7 g of diantimony trioxide [$Sb_2O_3$], and 5.8 g of cerium nitrate [$Ce(NO_3)_3\cdot 6H_2O$] were added to 2096 g of water, and the mixture was heated at 95° C. for 1 hour with stirring to prepare an aqueous mixed solution ($A_1$).

81.7 g of hydrogen peroxide water containing 30% by mass of $H_2O_2$ was added to 589.5 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 1188.6 g of silica sol containing 21.0% by mass of $SiO_2$ and having an average primary particle size of 9.0 nm was added, further 133.7 g of hydrogen peroxide water containing 30% by mass of $H_2O_2$ was added, and the mixture was continuously stirred at 55° C. for 30 minutes. Next, the aqueous mixed solution ($A_2$), 46.9 g of an aqueous ammonium metatungstate solution (purity: 50%), and a dispersion obtained by dispersing 230.4 g of powder silica having an average primary particle size of 12 nm in 2073.6 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average particle size of 54 μm.

The obtained dry powder ($D_1$) was subjected to the calcination step, the removal step, and the production step in the same way as in Example 1. The reaction yield of acrylonitrile (AN) is shown in Table 1.

Example 7

An oxide catalyst was produced in the same way as in Example 1 except that a mixing step given below was performed instead of the mixing step of Example 1. The reaction yield of acrylonitrile (AN) when the ammoxidation reaction of propane was performed in the same way as in Example 1 using this oxide catalyst is shown in Table 1.

(Mixing Step) Aqueous Mixed Solution ($B_1$)

The obtained aqueous mixed solution ($A_1$) was cooled to 70° C. Then, to this aqueous mixed solution, 1165.7 g of silica sol containing 21.0% by mass of $SiO_2$ and having an average primary particle size of 9.0 nm, and 109.1 g of hydrogen peroxide water containing 30% by mass of $H_2O_2$ were added, and the mixture was continuously stirred at 55° C. for 30 minutes. Next, the aqueous mixed solution ($A_2$), 38.3 g of an aqueous ammonium metatungstate solution (purity: 50%), and a dispersion obtained by dispersing 367.2 g of powder silica having an average primary particle size of 12 nm in 3304.8 g of water were added in this order to the aqueous mixed solution ($A_1$), and the mixture was then aged by stirring at 50° C. for 2.5 hours to obtain an aqueous mixed solution ($B_1$) in a slurry form.

Example 8

An oxide catalyst was produced in the same way as in Example 1 except that a mixing step given below was performed instead of the mixing step of Example 1. The reaction yield of acrylonitrile (AN) when the ammoxidation reaction of propane was performed in the same way as in Example 1 using this oxide catalyst is shown in Table 1.

(Mixing Step) Aqueous Mixed Solution ($B_1$)

The obtained aqueous mixed solution ($A_1$) was cooled to 70° C. Then, to this aqueous mixed solution, 1748.5 g of silica sol containing 21.0% by mass of $SiO_2$ and having an average primary particle size of 9.0 nm, and 109.1 g of hydrogen peroxide water containing 30% by mass of $H_2$ were added, and the mixture was continuously stirred at 55° C. for 30 minutes. Next, the aqueous mixed solution ($A_2$), 38.3 g of an aqueous ammonium metatungstate solution (purity: 50%), and a dispersion obtained by dispersing 244.8 g of powder silica having an average primary particle size of 12 nm in 2203.2 g of water were added in this order to the aqueous mixed solution ($A_1$), and the mixture was then aged by stirring at 50° C. for 2.5 hours to obtain an aqueous mixed solution ($B_1$) in a slurry form.

Example 9

(Preparation Step) Aqueous Mixed Solution ($A_1$)

481.4 g of ammonium heptamolybdate [$(NH_4)_6Mo_7O_{24} \cdot 4H_2O$], 66.8 g of ammonium metavanadate [$NH_4VO_3$], 94.1 g of diantimony trioxide [$Sb_2O_3$], and 5.4 g of cerium nitrate [$Ce(NO_3)_3 \cdot 6H_2O$] were added to 1822 g of water, and the mixture was heated at 95° C. for 1 hour with stirring to prepare an aqueous mixed solution ($A_1$).

56.5 g of hydrogen peroxide water containing 30% by mass of $H_2O_2$ was added to 407.7 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 1515.5 g of silica sol containing 21.0% by mass of $SiO_2$ and having an average primary particle size of 9.0 nm was added, further 109.6 g of hydrogen peroxide water containing 30% by mass of $H_2O_2$ was added, and the mixture was continuously stirred at 55° C. for 30 minutes. Next, the aqueous mixed solution ($A_2$), 34.4 g of an aqueous ammonium metatungstate solution (purity: 50%), and a dispersion obtained by dispersing 293.8 g of powder silica having an average primary particle size of 12 nm in 2643.8 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average particle size of 54 μm.

The obtained dry powder ($D_1$) was subjected to the calcination step, the removal step, and the production step in the same way as in Example 1. The reaction yield of acrylonitrile (AN) is shown in Table 1.

Example 10

(Preparation Step) Aqueous Mixed Solution ($A_1$)

688.9 g of ammonium heptamolybdate [$(NH_4)_6Mo_7O_{24} \cdot 4H_2O$], 90.7 g of ammonium metavanadate [$NH_4VO_3$], 135.7 g of diantimony trioxide [$Sb_2O_3$], and 10.3 g of cerium nitrate [$Ce(NO_3)_3 \cdot 6H_2O$] were added to 2489 g of water, and the mixture was heated at 95° C. for 1 hour with stirring to prepare an aqueous mixed solution ($A_1$).

96.7 g of hydrogen peroxide water containing 30% by mass of $H_2O_2$ was added to 697.5 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 861.8 g of silica sol containing 21.0% by mass of $SiO_2$ and having an average primary particle size of 9.0 nm was added, further 158.2 g of hydrogen peroxide water containing 30% by mass of $H_2O_2$ was added, and the mixture was continuously stirred at 55° C. for 30 minutes. Next, the aqueous mixed solution ($A_2$), 55.5 g of an aqueous ammonium metatungstate solution (purity: 50%), and a dispersion obtained by dispersing 167.0 g of powder silica having an average primary particle size of 12 nm in 1503.4 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average particle size of 54 μm.

The obtained dry powder ($D_1$) was subjected to the calcination step, the removal step, and the production step in the same way as in Example 1. The reaction yield of acrylonitrile (AN) is shown in Table 1.

Example 11

(Preparation Step) Aqueous Mixed Solution ($A_1$)

281.4 g of ammonium heptamolybdate [$(NH_4)_6Mo_7O_{24}\cdot 4H_2O$], 37.0 g of ammonium metavanadate [$NH_4VO_3$], 55.4 g of diantimony trioxide [$Sb_2O_3$], and 4.2 g of cerium nitrate [$Ce(NO_3)_3\cdot 6H_2O$] were added to 987 g of water, and the mixture was heated at 95° C. for 1 hour with stirring to prepare an aqueous mixed solution ($A_1$).

39.5 g of hydrogen peroxide water containing 30% by mass of $H_2O_2$ was added to 284.9 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 2109.7 g of silica sol containing 21.0% by mass of $SiO_2$ and having an average primary particle size of 9.0 nm was added, further 64.6 g of hydrogen peroxide water containing 30% by mass of $H_2O_2$ was added, and the mixture was continuously stirred at 55° C. for 30 minutes. Next, the aqueous mixed solution ($A_2$), 22.7 g of an aqueous ammonium metatungstate solution (purity: 50%), and a dispersion obtained by dispersing 409.0 g of powder silica having an average primary particle size of 12 nm in 3680.6 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average particle size of 54 μm.

The obtained dry powder ($D_1$) was subjected to the calcination step, the removal step, and the production step in the same way as in Example 1. The reaction yield of acrylonitrile (AN) is shown in Table 1.

Example 12

An oxide catalyst was produced in the same way as in Example 1 except that a mixing step given below was performed instead of the mixing step of Example 1. The reaction yield of acrylonitrile (AN) when the ammoxidation reaction of propane was performed in the same way as in Example 1 using this oxide catalyst is shown in Table 1.

(Mixing Step) Aqueous Mixed Solution ($B_1$)

The obtained aqueous mixed solution ($A_1$) was cooled to 70° C. Then, to this aqueous mixed solution, 2109.7 g of silica sol containing 21.0% by mass of $SiO_2$ and having an average primary particle size of 9.0 nm, and 109.1 g of hydrogen peroxide water containing 30% by mass of $H_2O_2$ were added, and the mixture was continuously stirred at 55° C. for 30 minutes. Next, the aqueous mixed solution ($A_2$), 38.3 g of an aqueous ammonium metatungstate solution (purity: 50%), and a dispersion obtained by dispersing 171.4 g of powder silica having an average primary particle size of 12 nm in 1542.2 g of water were added in this order to the aqueous mixed solution ($A_1$), and the mixture was then aged by stirring at 50° C. for 2.5 hours to obtain an aqueous mixed solution ($B_1$) in a slurry form.

Example 13

An oxide catalyst was produced in the same way as in Example 1 except that a mixing step given below was performed instead of the mixing step of Example 1. The reaction yield of acrylonitrile (AN) when the ammoxidation reaction of propane was performed in the same way as in Example 1 using this oxide catalyst is shown in Table 1.

(Mixing Step) Aqueous Mixed Solution ($B_1$)

The obtained aqueous mixed solution ($A_1$) was cooled to 70° C. Then, to this aqueous mixed solution, 757.7 g of silica sol containing 21.0% by mass of $SiO_2$ and having an average primary particle size of 9.0 nm, and 109.1 g of hydrogen peroxide water containing 30% by mass of $H_2O_2$ were added, and the mixture was continuously stirred at 55° C. for 30 minutes. Next, the aqueous mixed solution ($A_2$), 38.3 g of an aqueous ammonium metatungstate solution (purity: 50%), and a dispersion obtained by dispersing 452.9 g of powder silica having an average primary particle size of 12 nm in 4075.9 g of water were added in this order to the aqueous mixed solution ($A_1$), and the mixture was then aged by stirring at 50° C. for 2.5 hours to obtain an aqueous mixed solution ($B_1$) in a slurry form.

Example 14

(Preparation Step) Aqueous Mixed Solution ($A_1$)

478.5 g of ammonium heptamolybdate [$(NH_4)_6Mo_7O_{24}\cdot 4H_2O$], 68.7 g of ammonium metavanadate [$NH_4VO_3$], 86.4 g of diantimony trioxide [$Sb_2O_3$], and 7.2 g of cerium nitrate [$Ce(NO_3)_3\cdot 6H_2O$] were added to 1873 g of water, and the mixture was heated at 95° C. for 1 hour with stirring to prepare an aqueous mixed solution ($A_1$).

66.5 g of hydrogen peroxide water containing 30% by mass of $H_2O_2$ was added to 480.1 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 1515.5 g of silica sol containing 21.0% by mass of $SiO_2$ and having an average primary particle size of 9.0 nm was added, further 100.7 g of hydrogen peroxide water containing 30% by mass of $H_2O_2$ was added, and the mixture was continuously stirred at 55° C. for 30 minutes. Next, the aqueous mixed solution ($A_2$), 38.5 g of an aqueous ammonium metatungstate solution (purity: 50%), and a dispersion obtained by dispersing 293.8 g of powder silica having an average primary particle size of 12 nm in 2643.8 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average particle size of 54 μm.

The obtained dry powder ($D_1$) was subjected to the calcination step, the removal step, and the production step in the same way as in Example 1. The reaction yield of acrylonitrile (AN) is shown in Table 1.

Example 15

(Preparation Step) Aqueous Mixed Solution ($A_1$)

430.8 g of ammonium heptamolybdate [$(NH_4)_6Mo_7O_{24} \cdot 4H_2O$], 61.8 g of ammonium metavanadate [$NH_4VO_3$], 144.3 g of diantimony trioxide [$Sb_2O_3$], and 4.7 g of cerium nitrate [$Ce(NO_3)_3 \cdot 6H_2O$] were added to 1681 g of water, and the mixture was heated at 95° C. for 1 hour with stirring to prepare an aqueous mixed solution ($A_1$).

50.6 g of hydrogen peroxide water containing 30% by mass of $H_2O_2$ was added to 364.8 g of the niobium mixed solution ($B_0$) having an oxalic acid/niobium molar ratio of 2.340, and the mixture was mixed by stirring at room temperature for 10 minutes to prepare an aqueous mixed solution ($A_2$).

(Mixing Step) Aqueous Mixed Solution ($B_1$)

The obtained aqueous mixed solution ($A_1$) was cooled to 70° C. Then, to this aqueous mixed solution, 1515.5 g g of silica sol containing 21.0% by mass of $SiO_2$ and having an average primary particle size (9 nm) described in Table 1 was added, further 168.1 g of hydrogen peroxide water containing 30% by mass of $H_2O_2$ was added, and the mixture was continuously stirred at 55° C. for 30 minutes. Next, the aqueous mixed solution ($A_2$), 31.3 g of an aqueous ammonium metatungstate solution (purity: 50%), and a dispersion obtained by dispersing 293.8 g of powder silica having an average primary particle size of 12 nm in 2643.8 g of water were added in this order to the aqueous mixed solution ($A_1$), and the mixture was then aged by stirring at 50° C. for 2.5 hours to obtain an aqueous mixed solution ($B_1$) in a slurry form.

(Drying Step) Dry Powder ($C_1$)

The obtained aqueous mixed solution ($B_1$) was supplied to a centrifugal spray dryer and dried to obtain a dry powder ($C_1$) in a microsphere form. The inlet temperature of the dryer was 210° C., and the outlet temperature was 120° C.

The obtained dry powder ($C_1$) was classified using a sieve with openings of 25 μm to obtain a dry powder ($D_1$) as a classified product. The obtained dry powder ($D_1$) contained 0.2% by mass of 25 μm or smaller particles and had an average particle size of 54 μm.

The obtained dry powder ($D_1$) was subjected to the calcination step, the removal step, and the production step in the same way as in Example 1. The reaction yield of acrylonitrile (AN) is shown in Table 1.

Example 16

An oxide catalyst was produced in the same way as in Example 1 except that 1515.5 g of the silica sol having an average primary particle size of 9.0 nm in Example 1 was changed to a mixture of 1212.4 g of silica sol containing 21.0% by mass of $SiO_2$ and having an average primary particle size of 9.0 nm, and 303.1 g of silica sol containing 21.0% by mass of $SiO_2$ and having an average primary particle size of 14.0 nm. The reaction yield of acrylonitrile (AN) when the ammoxidation reaction of propane was performed in the same way as in Example 1 using this oxide catalyst is shown in Table 1.

Example 17

An oxide catalyst was produced in the same way as in Example 1 except that 1515.5 g of the silica sol having an average primary particle size of 9.0 nm in Example 1 was changed to a mixture of 757.8 g of silica sol containing 21.0% by mass of $SiO_2$ and having an average primary particle size of 7.0 nm, and 757.8 g of silica sol containing 21.0% by mass of $SiO_2$ and having an average primary particle size of 14.0 nm. The reaction yield of acrylonitrile (AN) when the ammoxidation reaction of propane was performed in the same way as in Example 1 using this oxide catalyst is shown in Table 1.

Comparative Example 1

An oxide catalyst was produced in the same way as in Example 1 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

Comparative Example 2

An oxide catalyst was produced in the same way as in Example 1 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

Comparative Example 3

An oxide catalyst was produced in the same way as in Example 9 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

Comparative Example 4

An oxide catalyst was produced in the same way as in Example 9 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

Comparative Example 5

An oxide catalyst was produced in the same way as in Example 14 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

Comparative Example 6

An oxide catalyst was produced in the same way as in Example 15 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

Comparative Example 7

An oxide catalyst was produced in the same way as in Example 15 except that the silica sol having an average primary particle size of 9.0 nm in Example 1 was changed to silica sol having an average primary particle size described in Table 1. The reaction yield of acrylonitrile (AN) when the ammoxidation reaction of propane was performed in the same way as in Example 1 using this oxide catalyst is shown in Table 1.

TABLE 1

| | Silica sol | | | Oxide catalyst | | | | | | | |
|---|---|---|---|---|---|---|---|---|---|---|---|
| | (Physical property 3) Average primary particle size [nm] | (property 3) Content thereof having primary particle size of smaller than 11 nm [%] | (Physical property 3) Silica sol content [% by mass] | (Physical property 4) Composition $Mo_1V_aSb_bNb_cW_dCe_e$ | | | | | | (Physical property 5) Amount of support [% by mass] | (Evaluation) Yield [%] |
| | | | | a | b | c | d | e | (a/b) | | |
| Example 1 | 9.0 | 74 | 52 | 0.190 | 0.228 | 0.120 | 0.034 | 0.007 | 0.833 | 51 | 55.3 |
| Example 2 | 7.0 | 91 | 52 | | | | | | | 51 | 54.3 |
| Example 3 | 10.5 | 62 | 52 | | | | | | | 51 | 55 |
| Example 4 | 3.0 | 98 | 52 | | | | | | | 51 | 53.7 |
| Example 5 | 9.0 | 74 | 52 | | | | | | | 60 | 54.7 |
| Example 6 | 9.0 | 74 | 52 | | | | | | | 40 | 54.6 |
| Example 7 | 9.0 | 74 | 40 | | | | | | | 51 | 54.8 |
| Example 8 | 9.0 | 74 | 60 | | | | | | | 51 | 55.4 |
| Example 9 | 9.0 | 74 | 52 | 0.207 | 0.219 | 0.102 | 0.030 | 0.005 | 0.945 | 51 | 56.2 |
| Example 10 | 9.0 | 74 | 52 | 0.190 | 0.228 | 0.120 | 0.034 | 0.007 | 0.833 | 29 | 53.8 |
| Example 11 | 9.0 | 74 | 52 | | | | | | | 71 | 53.7 |
| Example 12 | 9.0 | 74 | 72 | | | | | | | 51 | 54.4 |
| Example 13 | 9.0 | 74 | 26 | | | | | | | 51 | 54.1 |
| Example 14 | 9.0 | 74 | 52 | 0.207 | 0.209 | 0.120 | 0.030 | 0.007 | 0.990 | 51 | 54.5 |
| Example 15 | 9.0 | 74 | 52 | 0.207 | 0.284 | 0.102 | 0.030 | 0.005 | 0.729 | 51 | 55.6 |
| Example 16 | 9.0 + 14.0 (= 10.2) | 61 | 52 | 0.190 | 0.228 | 0.120 | 0.034 | 0.007 | 0.833 | 51 | 54.4 |
| Example 17 | 9.0 + 14.0 (= 10.5) | 58 | 52 | | | | | | | 51 | 54.2 |
| Comparative Example 1 | 14.0 | 9.9 | 52 | | | | | | | 51 | 53.6 |
| Comparative Example 2 | 2.0 | 99 | 52 | | | | | | | 51 | 52.9 |
| Comparative Example 3 | 14.0 | 9.9 | 52 | 0.207 | 0.219 | 0.120 | 0.030 | 0.005 | 0.945 | 51 | 54.7 |
| Comparative Example 4 | 2.0 | 99 | 52 | | | | | | | 51 | 53.3 |
| Comparative Example 5 | 14.0 | 9.9 | 52 | 0.207 | 0.209 | 0.120 | 0.030 | 0.007 | 0.990 | 51 | 52.8 |
| Comparative Example 6 | 14.0 | 9.9 | 52 | 0.207 | 0.284 | 0.102 | 0.030 | 0.005 | 0.729 | 51 | 52 |
| Comparative Example 7 | 10.0 | 51 | 52 | 0.19 | 0.228 | 0.12 | 0.034 | 0.007 | 0.833 | 51 | 53.5 |

The present application is based on Japanese Patent Application No. 2015-073794 filed in the Japan Patent Office on Mar. 31, 2015, the contents of which are incorporated herein by reference.

What is claimed is:

1. A method for producing an oxide catalyst comprising Mo, V, Sb, and Nb for use in a gas-phase catalytic oxidation reaction or a gas-phase catalytic ammoxidation reaction of propane or isobutane, the method comprising:
   a preparation step of preparing a first aqueous mixed solution containing Mo, V, and Sb;
   a mixing step of mixing the first aqueous mixed solution with a support raw material comprising silica sol, and a Nb raw material to obtain a second aqueous mixed solution;
   a drying step of drying the second aqueous mixed solution to obtain a dry powder; and
   a calcination step of calcining the dry powder to obtain the oxide catalyst, wherein
   the support raw material comprises 25% by mass or more, based on $SiO_2$, of the silica sol having an average primary particle size of 3.0 nm or larger and smaller than 11 nm based on a total amount of the support raw material, and the silica sol comprises 55% or more of silica sol particles having a primary particle size of smaller than 11 nm.

2. The method for producing the oxide catalyst according to claim 1, wherein the oxide catalyst has a composition represented by following formula (1):

$$MoV_aSb_bNb_cZ_dO_n \qquad (1)$$

wherein Z represents at least one element selected from the group consisting of W, La, Ce, Yb, and Y; a, b, c, and d represent values in ranges of $0.01 \leq a \leq 0.35$, $0.01 \leq b \leq 0.35$, $0.01 \leq c \leq 0.20$, and $0.00 \leq d \leq 0.10$, respectively; and n represents a value that satisfies balance among valences.

3. The method for producing the oxide catalyst according to claim 2, wherein in the formula (1), (a/b) is 0.50 or more and 0.98 or less.

4. The method for producing the oxide catalyst according to claim 1, wherein the oxide catalyst comprises 30% by mass or more and 70% by mass or less of a support based on the total amount of the oxide catalyst.

5. The method for producing the oxide catalyst according to claim 1, wherein the support raw material further comprises powder silica.

6. The method for producing the oxide catalyst according to claim 1, wherein the support raw material comprises 30% by mass or more and 70% by mass or less, based on $SiO_2$, of the silica sol based on the total amount of the support raw material.

7. A method for producing unsaturated nitrile, comprising a production step of producing unsaturated nitrile by a gas-phase catalytic ammoxidation reaction of propane or isobutane in presence of an oxide catalyst comprising Mo, V, Sb, and Nb for use in a gas-phase catalytic oxidation reaction or a gas-phase catalytic ammoxidation reaction of propane or isobutane, and
   wherein the oxide catalyst is prepared by a method comprising:
   a preparation step of preparing a first aqueous mixed solution containing Mo, V, and Sb;
   a mixing step of mixing the first aqueous mixed solution with a support raw material comprising silica sol, and a Nb raw material to obtain a second aqueous mixed solution;
   a drying step of drying the second aqueous mixed solution to obtain a dry powder; and
   a calcination step of calcining the dry powder to obtain the oxide catalyst, wherein
   the support raw material comprises 25% by mass or more based on $SiO_2$, of the silica sol having an average primary particle size of 3.0 nm or larger and smaller than 11 nm based on a total amount of the support raw material, and the silica sol comprises 55% or more of silica sol particles having a primary particle size of smaller than 11 nm.

* * * * *